United States Patent [19]
Heine

[11] 3,936,161
[45] Feb. 3, 1976

[54] OPHTHALMOSCOPE ILLUMINATION ARRANGEMENT

[75] Inventor: Helmut A. Heine, Herrsching, Upper Bavaria, Germany

[73] Assignees: Propper Manufacturing Company, Inc., Long Island City, N.Y.; Optotechnik Heine KG, Herrsching, Upper Bavaria, Germany

[22] Filed: Aug. 14, 1974

[21] Appl. No.: 497,187

[52] U.S. Cl. ................................. 351/6; 351/12
[51] Int. Cl.² ........................................ A61B 3/12
[58] Field of Search ........... 351/6, 9, 10, 11, 12, 13, 351/16

[56] References Cited
UNITED STATES PATENTS

| | | | |
|---|---|---|---|
| 1,776,960 | 9/1930 | Turville et al. | 351/16 X |
| 1,981,214 | 11/1934 | Allyn | 351/11 X |
| 2,726,570 | 12/1955 | Thorburn | 351/16 X |

*Primary Examiner*—Paul A. Sacher
*Attorney, Agent, or Firm*—Amster & Rothstein

[57] ABSTRACT

This application discloses an ophthalmoscope illumination arrangement including a bulb mounted in a special bulb carrier which is adapted to cooperate with the ophthalmoscope chassis so as to automatically position the bulb for best illumination. The bulb carrier and ophthalmoscope chassis cooperate to establish the longitudinal position of the bulb filament along the illumination axis of the instrument and to align the rotational position of the bulb filament with the upper edge of the reflective mirror or prism so that the illumination beam is in close alignment with the viewing axis of the instrument.

3 Claims, 9 Drawing Figures

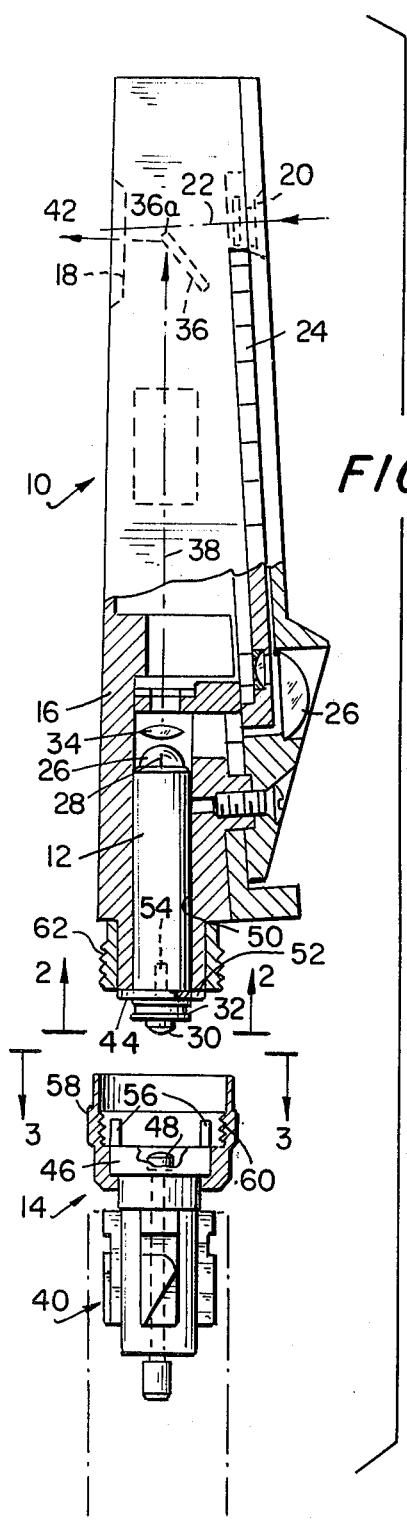
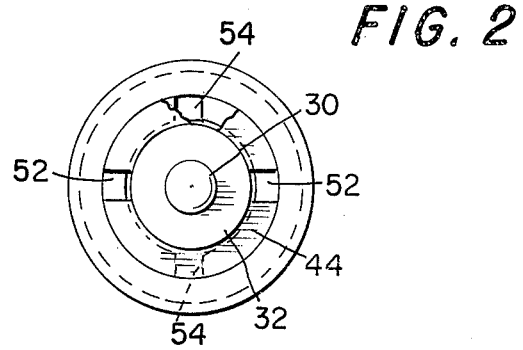
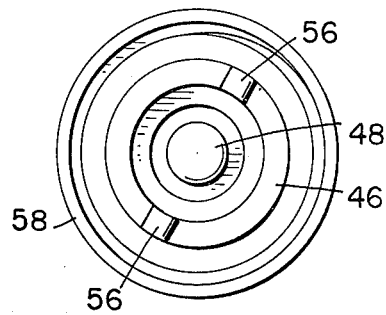
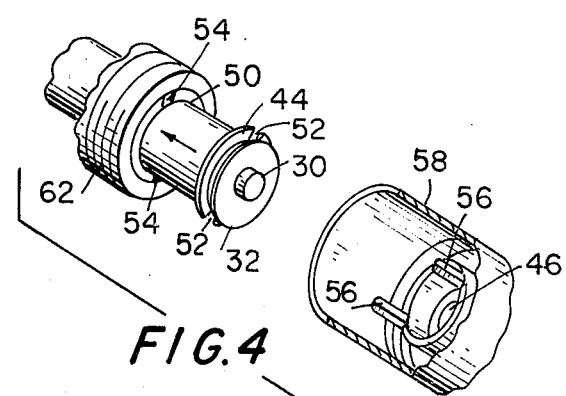
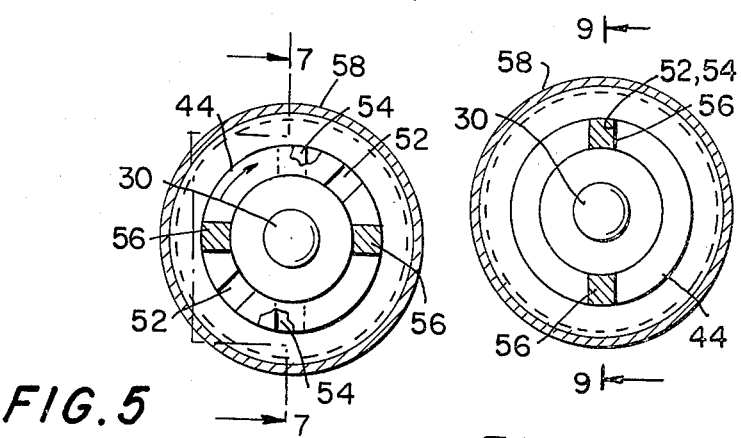
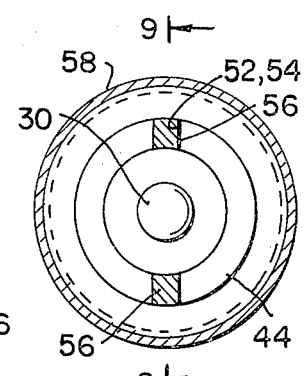

OPHTHALMOSCOPE ILLUMINATION ARRANGEMENT

This invention relates generally to medical diagnostic instruments and more specifically to an illumination arrangement for use in ophthalmoscopes.

Conventional ophthalmoscopes (the instrument with which the doctor examines the eye) include an adjustable lens arrangement through which the doctor views the interior of the eye and an illuminating system which projects a beam of light into the eye. In modern conventional ophthalmoscopes, the illumination beam is directed into the eye by a mirror placed immediately below the viewing axis (or doctor's line of sight) through the instrument such that the mirror reflects illumination from the bulb into the patient's eye. It is desirable in such systems that the viewing axis be as nearly as possible coincident with the projected beam, i.e., that the angle between the axis and the beam be as small as possible and that the origin of the axis and beam be as close as possible.

To accomplish this, applicant has found it desirable in an ophthalmoscope wherein a conventional incadescent bulb is used to position the bulb within the instrument such that the bulb filament is in alignment with the upper edge of the mirror. This requires the accurate positioning of the illumination bulb within the ophthalmoscope chassis such that the rotational position of the filament is aligned parallel to the upper mirror edge. Applicant has also found it desirable to control the distance between the filament and the mirror to provide proper focus of the filament as known in the art. While it would be a relatively simple matter matter to permanently position the bulb in this desired location, the matter is substantially complicated by the fact that the bulb requires periodic replacement by the physician or user. In the bulb systems of present instruments, it is difficult to properly position the bulb filament to obtain the desired alignment of the filament with the upper edge of the mirror and the proper focus of the filament.

It is thus an object of the present invention to provide an illumination arrangement for opthalmoscopes wherein a replaceable illumination bulb is properly positioned to provide a maximum illumination beam as close as possible to the viewing axis of the instrument. A related object of the present invention is to provide a bulb-carrier system wherein the rotational and lateral position of the bulb filament are automatically established whenever the bulb is inserted without the specific attention of the person inserting the bulb.

In accomplishing these and other objects in accordance with the present invention, applicant's ophthalmoscope includes an ophthalmoscope chassis having a bulb-receiving sleeve adapted to cooperate with a specially prepared bulb-carrier arrangement. The bulb carrier includes a lateral stop, with the distance between the stop and the bulb filament being predetermined during manufacture. The bulb carrier also includes a guide slot or other guide means adapted to cooperate with a guide arrangement on the ophthalmoscope, with the alignment of the filament and the bulb-carrier guide being established during manufacture of the bulb carrier. The system preferably also includes a screw cap or other means for securing the bulb in position, which automatically rotates the bulb carrier to its proper position as the bulb cap is secured over the bulb.

Further objects, features and advantages of the present invention will be appreciated by reference to the following detailed description of a presently preferred embodiment of the invention when taken in conjunction with the appended drawings wherein:

FIG. 1 is a cross-sectional view of an ophthalmoscope head in accordance with the invention with the bulb carrier in place and with the bulb locking cap removed;

FIG. 2 is a view taken along line 2—2 in FIG. 1 looking in the direction of the arrows;

FIG. 3 is a view taken along line 3—3 in FIG. 1 looking in the direction of the arrows;

FIG. 4 is a prospective view showing the bulb carrier being inserted in the ophthalmoscope head with the bulb cap removed;

FIG. 5 is a cross-sectional view taken approximately at the position of line 2—2 in FIG. 1 with the bulb cap advanced upwardly against the bulb carrier;

FIG. 6 is a view similar to FIG. 5 with the bulb carrier aligned and with the bulb cap fully inserted;

Figure 7:
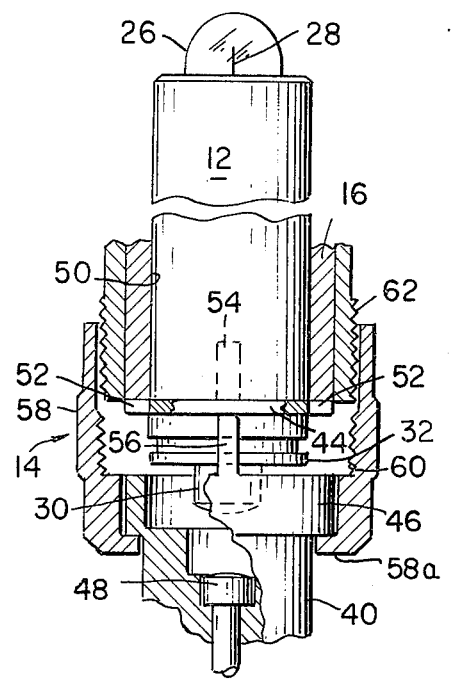
FIG. 7 is a cross-sectional view partially broken away taken on line 7—7 in FIG. 5.

FIG. 1 generally shows an ophthalmoscope head 10 in accordance with the preferred embodiment having inserted therein applicant's bulb carrier 12 with the bulb closing cap 14 and handle mounting unit 40 removed.

The general operation of ophthalmoscope head 10 is well-known in the art and will not be described herein in greater detail than required for an understanding of applicant's present invention. Basically, the ophthalmoscope head includes a chassis 16 including forward and rearward apertures 18, 20 respectively through which the doctor observes the eye. The doctor's line of sight (also referred to herein as the viewing axis) passes through apertures 18 and 20 and is identified in FIG. 1 by the numeral 22. The ophthalmoscope head includes a lens wheel 24 adapted to carry a series of lenses of different powers so that the doctor can obtain a sharp focus of the fundus or other portion of the eye. A viewing lens window 26 is also provided so that the power of the lens in position along viewing axis 22 can be determined. The operation of lens wheel 24 and the viewing arrangement 26 is well-known in the art.

In addition to providing lenses in the viewing axis 22, ophthalmoscope 10 is adapted to project an illuminating light beam into the eye. The illumination beam is generated by lamp envelope 26 enclosing a conventional lamp filament 28. As to be described in more detail hereinafter, the bulb envelope is permanently mounted in bulb carrier 12 which has a positive electrical contact pin 30 and a negative electrical contact ring 32 at its lower end. Light from the bulb is focused by means of a condensing lens 34 and is reflected by mirror 36 into the eye. As shown in the art, other lenses, masks or other optical stations may be positioned along the path of light from the bulb (sometimes referred to herein as the illuminating axis) shown as axis 38 in FIG. 1.

Closing cap 14 is adapted to cover and securely retain bulb 12 in position within the ophthalmoscope chassis in a manner to be described in more detail hereinafter. Cap 14 is formed integrally with a mounting bayonet 40, which, as shown in FIG. 1, is a conventional arrangement for mounting head 10 to a battery handle or other device. It will be understood that there are numerous other standard mounting arrangements known in the art and that other connector arrangements may be incorporated into applicant's invention. Negative contact ring 32 is adapted to make electrical contact with negative contact 46 in cap 14. Positive contact pin 30 makes positive electrical contact with pin 48 in cap 14, pin 48 being electrically isolated from the negative contact surface 46. Pin 48 and negative contact surface 46 are adapted to make contact through connector 40 in well-known fashion with the positive and negative terminals of an appropriate power supply.

As indicated above, it has been found desirable to bring the light beam reflected from mirror 36 (as represented, for example, by arrow 42 in FIG. 1) in as close coincidence as possible with the viewing axis 22. This is accomplished by aligning the bulb filament 28 in such a way that the filament is parallel to the upper edge 36a of mirror 36. It is also desirable to position the bulb such that filament 28 is focused at a predetermined point as known in the art. Proper alignment of bulb filament 28 thus includes two components: the distance between the filament and the mirror 36 must be controlled; and the rotational position of the filament must be established.

The first condition is established in accordance with applicant's invention by permanently fixing bulb envelope 26 in cylindrical bulb carrier 12. Bulb carrier 12 is provided with a rear ledge 44 best seen in FIG. 4. Ledge 44 is conveniently formed as part of the negative contact ring 12. Bulb carrier 12 is adapted to be received within sleeve 50 which is formed in the lower or neck portion of ophthalmoscope chassis 16. When bulb carrier 12 is in position, contact ledge 44 abuts directly against the lower end of sleeve 50. The distance between ledge 44 and the filament 28 is preset in manufacture such that abutment of ledge 44 against the lower surface of sleeve 50 positions filament 28 at an appropriate distance from mirror 36.

To establish the rotational position of carrier 12, the rear ledge 44 is provided with two slots 52, and sleeve 50 is similarly provided with two corresponding slots 54. These slots are shown in FIGS. 2 and 4. Cap 14 includes a pair of aligning lugs 56 (conveniently made integral with negative contact 46) adapted to be received within slots 52 and 54.

Figure 9:
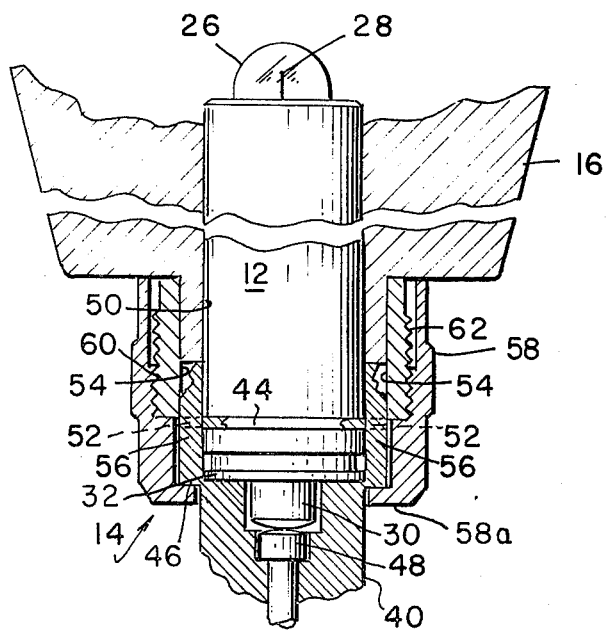
FIG. 9 is a cross-sectional view taken along line 9—9 in FIG. 6.

The ophthalmoscope chassis 16, bulb carrier 12 and bulb cap 14 assembly is shown in its fully assembled condition in FIG. 9. As will be appreciated by reference to FIG. 9 (in combination with FIG. 1), the bulb cap assembly 14 includes a cylindrical cover member 58, the lower portion of which 58a turns inwardly to retain negative contact 46 in position. Cover 58 includes internal threads 60 which start interior of the upper lip of the cover 58. In the fully assembled position shown in FIG. 9, threads 60 mate with external thread 62 which surround the lower neck portion of chassis 16. In this fully closed position, positioning lugs 56 extend through slots 52 in member 44 and into slots 54 in sleeve 50. The rotational position of the bulb carrier assembly 12 and hence of filament 28 is thus fixed in the desired aligned position.

Applicant's arrangement as discribed above and as explained hereafter is uniquely adapted to automatically position the bulb carrier assembly as cap 14 is applied so that the bulb is automatically and correctly aligned as the cap is screwed onto the neck.

Specifically, assume the bulb carrier is inserted in a random position, for example, the position shown in FIG. 5 with slots 52 out of alignment with slots 54 (and hence filament 28 out of alignment with mirror edge 36a). The cap 14 is then positioned over the bulb neck assembly (as also shown in FIG. 5) with pins 56 in a third random position, for example, out of alignment with both slots 52 and 54. In this position, pins 56 sit on ledge 44 as seen in FIG. 7. Cover 58 is maintained in approximate proper orientation on the chassis neck by the forward portion of cover 58 (which does not include threads). The length of pins 56 and the depth of threads 60 are selected such that in this position, threads 60 do not engage the mating threads 62 on the chassis neck.

Figure 8:
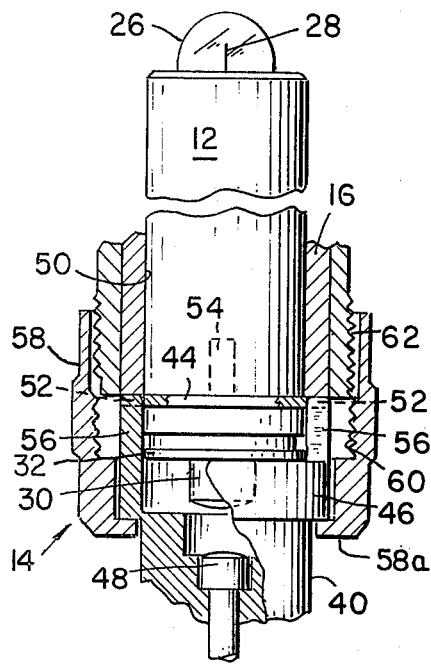
FIG. 8 is a cross-sectional view similar to FIG. 7, but showing the cap rotated to engage the bulb carrier.

The user then rotates cap 14 attempting to screw the cap to the neck. In grasping unit 14, the fingers naturally grasp both the jacket 58 and the connector member 40. The unitary connector 40 — negative contact member 46 combination is free to rotate within cover 58. However, when grasped naturally and rotated, the cover 58 and connector — negative contact element tend to rotate together unless the connector — negative contact element is stopped. As the assembly 14 is rotated, pin 56 thus moves around ledge 44 until it falls into slots 52. The forward end of pin 56 is preferably rounded so that it easily fits into slot 52. The condition is shown in FIG. 8. Note that in this position, threads 60 and 62 still do not mate.

As cap 14 continues to be turned with pins 56 in slots 52, the bulb carrier 12 turns with the cap until the pins 56 eventually reach slot 54 in sleeve 50. As pins 56 are received in slot 54, the connector – negative contact element is precluded from rotating. However, cover 58 continues to turn, and at this point the threads 60 and 62 engage so that continued turning motion draws pins 56 fully into slots 54. Note that at this point, bulb assembly 12 has been properly positioned so that filament 28 is aligned with mirror edge 36a.

Alignment of all three elements occurs in no more than one revolution of member 14 and usually substantially less. Applicant has found that with this arrangement, the person inserting the bulb and applying cap 14 is usually not even aware of the fact that application of the cap has also rotationally aligned the bulb. With this arrangement, the cap assembly cannot be applied unless the bulb is in proper alignment and the alignment of the bulb occurs automatically as one attempts to apply the cap without the operator taking any special precautions.

It will be appreciated that the above detailed description is merely representative of the application of the present invention. Numerous other embodiments will occur to those skilled in the art without departing from the spirit or scope of the present invention as defined by the following claims.

What is claimed is:

1. An ophthalmoscope comprising an ophthalmoscope chassis defining a bulb-receiving sleeve therein, a bulb carrier shaped to be received within said sleeve, said carrier including stop means with the distance between the filament of said bulb and said stop means being predetermined to establish the longitudinal position of said filament in said chassis, rotational guide means associated with said sleeve and corresponding rotational guide means associated with said carrier, alignment of said guide means establishing the rotational position of said carrier with said sleeve, said guide means being fixed with respect to said filament so that alignment of said guide means establishes the rotational position of said filament within said chassis to provide most effective illumination, and closure means positioned over said sleeve for securing said carrier within said sleeve, said closure means including rotational guide means engaging the rotational guide means of said sleeve and said carrier, said closure means rotating over said sleeve on attachment thereof to sequentially engage the guide means of said carrier and the guide means of said sleeve to automatically rotate said carrier into proper position as said closure means is attached.

2. Apparatus in accordance with claim 1 wherein said rotational guide means on said sleeve comprises at least one slot in said sleeve, said rotational guide means on said carrier comprises a flange on said carrier including at least one corresponding slot on said flange and said rotational guide means on said closure comprises at least one corresponding guide pin adapted to be received within said guide slots when said carrier is in proper rotational position.

3. Apparatus in accordance with claim 2 wherein said ophthalmoscope chassis includes threads adjacent said bulb-receiving sleeve and said closure means contains threads mating to said ophthalmoscope chassis threads, said threads being positioned such that engagement of said threads is prevented until said sleeve is in the desired rotational position.

* * * * *